United States Patent
Müller et al.

(10) Patent No.: US 7,377,943 B2
(45) Date of Patent: May 27, 2008

(54) SURFACE TREATED METALLIC IMPLANT AND BLASTING MATERIAL

(75) Inventors: Wolf-Dieter Müller, Berlin (DE); Georg Berger, Zepernick (DE)

(73) Assignees: Humboldt-Universitaet Berlin, Charite Universitaetsklinikum (DE); BAM Bundesanstalt fuer Materialforschung und - pruefung (DE)

( * ) Notice: Subject to any disclaimer, the term of this patent is extended or adjusted under 35 U.S.C. 154(b) by 829 days.

(21) Appl. No.: 10/480,918

(22) PCT Filed: Jun. 14, 2002

(86) PCT No.: PCT/DE02/02229

§ 371 (c)(1), (2), (4) Date: Dec. 15, 2003

(87) PCT Pub. No.: WO02/102431

PCT Pub. Date: Dec. 27, 2002

(65) Prior Publication Data

US 2004/0158330 A1    Aug. 12, 2004

(30) Foreign Application Priority Data

Jun. 15, 2001   (DE) ................ 101 29 843

(51) Int. Cl.
*A61K 2/28* (2006.01)
*B24D 3/02* (2006.01)
*C09C 1/68* (2006.01)
*C09K 3/14* (2006.01)
*A61K 2/00* (2006.01)
*A61K 6/083* (2006.01)

(52) U.S. Cl. ................ 623/23.56; 623/23.57; 623/23.6; 523/115; 51/309

(58) Field of Classification Search ............ 623/23.56, 623/23.57, 23.6; 523/115, 116; 51/309
See application file for complete search history.

(56) References Cited

U.S. PATENT DOCUMENTS

| 6,767,854 B2 * | 7/2004 | Berger et al. ................ 501/10 |
| 7,109,254 B2 * | 9/2006 | Muller et al. ............... 523/105 |
| 7,223,808 B2 * | 5/2007 | Muller et al. ............... 524/414 |

FOREIGN PATENT DOCUMENTS

| DE | 41 26 800 A1 | 2/1993 |
| DE | 197 44 809 C1 | 7/1999 |
| EP | 0 541 546 B1 | 11/1990 |
| GB | 2 199 028 A | 12/1987 |
| WO | 87/07357 | 5/1991 |
| WO | 91/07357 | 5/1991 |

OTHER PUBLICATIONS

Biomaterials 12, "Bioactive Glass Ceramics: Properties and Applications", 1991, pp. 155-163.
Biomaterials 18, "Solubility of Compositions in the System . . . ", 1997, pp. 1671-1675.
4th World Biomaterials Congress, Apr. 24, 1992, p. 33.
Key Engineering Materials, "Hydroxyapatite's Solubility May Cause Loosening of Coated Implants", vol. 192-195, pp. 111-114.

* cited by examiner

*Primary Examiner*—Thomas J Sweet
(74) *Attorney, Agent, or Firm*—Akerman Senterfitt; Stephan A. Pendorf; Gregory M. Lefkowitz

(57) ABSTRACT

The invention relates to a metallic implant, which has vitreous-crystalline bioactive material on the surface thereof. According to the invention, a metallic implant base body arranged on the surface of the particles has a bioactive, vitreous-crystalline material consisting of 15-45 wt. % CaO, 40-45 wt. % $P_2O_5$, 10-40 wt. % $ZrO_2$ and 0.7-3.5 wt. % fluoride, having apatite and calcium zirconium phosphate as main crystalline and a glass phase as an auxiliary component. Said vitreous crystalline material contains at least 35 wt. % main crystal phases and at least 5-15 wt. % auxiliary compounds. All of the percentage data is expressed in relation to the total weight of the vitreous crystalline material and the particle size of the vitreous crystalline material is between 60-350 μm.

16 Claims, No Drawings

SURFACE TREATED METALLIC IMPLANT AND BLASTING MATERIAL

CROSS REFERENCE TO RELATED APPLICATION

This application is a national stage of PCT/DEO2/02229 filed June 14, 2002, and based upon DE 101 29 843.9 filed June 15, 2001 under the International Convention.

FIELD OF THE INVENTION

The present invention relates to a metallic implant which has vitreous-crystalline bioactive material on the surface thereof as well as to a blasting material for treating said surface.

BACKGROUND TO THE INVENTION

Inorganic materials with long-term stability are known per se. Materials which are specifically used as bioactive bone-replacement materials and have a sufficient long-term stability are also described in the relevant literature. For example, there have been numerous publications dedicated to the successful clinical use of glass ceramics and/or sintered glass ceramics with the main crystal phases apatite and wollastonite [Kokubo, T., Biomaterials, 12 (1991) 155-163; Berger, G. et al.: Long-term stable bioactive glass ceramics as an implant material—ten years of clinical experience, Fourth World Biomaterial Congress, Berlin, Apr. 24-28, 1992, Transactions p. 33]. The chemical stability of the aforesaid materials was surpassed by other bioactive materials based on calcium-zirconium/titanium phosphate which can only be produced by means of ceramic methods, but do not form a melt at temperatures which are common in the glass industry (approximately 1,650° C.), which, as is known, brings about disadvantages as regards the mechanical stability of such granulated materials and in particular of molded bodies manufactured therefrom (Biomaterials 18 (1997) 1671-1675).

Furthermore, it is known that metallic implants are roughened on their surface in order to improve bonding to the surrounding tissue. During this blasting operation, particles are always incorporated into the metallic surface owing to tribochemical reactions.

Commonly, commercial methods relate to blasting with $Al_2O_3$. The roughening effect on the surface is very good, whereas the concentration of $Al_2O_3$ on the surface is problematic from the aspect of biocompatibility. An improvement was achieved through the use of glass-ceramic materials which contain apatite and wollastonite or apatite, wollastonite and $Ca_7Mg_2P_2O_{24}$ as main crystal phase as described in DE 41 26 800 A1. Here, particles with a thickness of at least 1 μm are incorporated into the surface of the implant at a hardness according to Mohs of 5-7° of the vitreous-crystalline or ceramic materials. The roughness of the surface thus created ranges between 5 and 10 μm.

The chemical long-term stability of the aforesaid materials in connection with their bioactivity (direct connective tissue-free bone contact) has so far been regarded as unsurpassed.

Long-term stable commercial materials are derived from apatites. They are either ceramics with hydroxyapatites or fluoroapatites (HAp, FAp) as main crystal phase and with poor processing properties or they are glass ceramics which in most cases include another crystal phase, e.g. wollastonite for achieving improved mechanical properties, mica phases for achieving machinability, etc. The processing properties of glass ceramics are in general considered to be sufficient. Seen from the aspect of long-term stability, the known combinations of apatites, further crystal phases and/or residual glass components always result in materials whose solubility is higher than that of the pure phases (HAp, FAp).

SUMMARY OF THE INVENTION

The object of the invention is to provide a metallic implant with a roughened surface which carries a bioactive material and has, at the same time, an improved chemical stability.

According to the invention, a surface-treated metallic implant is provided wherein a metallic implant base body has on its surface particles of a bioactive, vitreous-crystalline material consisting of 15-45 wt.-% CaO, 40-45 wt.-% $P_2O_5$, 10-40 wt.-% $ZrO_2$ and 0.7-3.5 wt.-% fluoride, said material containing apatite and calcium zirconium phosphate as main crystal phases and a glass phase as an auxiliary component, wherein the main crystal phases jointly make up at least 35 wt.-% and the auxiliary components make up 5-15 wt.-% and wherein all percentage data are expressed in relation to the total weight of the vitreous-crystalline material.

DETAILED DESCRIPTION

A preferred vitreous-crystalline material contains 23-39 wt.-% CaO, 40-45 wt.-% $P_2O_5$, 20-35 wt.-% $ZrO_2$ and 1-3 wt.-% fluoride, containing apatite and calcium zirconium phosphate as main crystal phases and a glass phase as an auxiliary component, wherein the main crystal phases jointly make up at least 35 wt.-% and the auxiliary components make up 5-15 wt.-%.

Another preferred vitreous-crystalline material contains 23-39 wt.-% CaO, 40-45 wt.-% $P_2O_5$, 20-35 wt.-% $ZrO_2$ and 1-3 wt.-% fluoride and in addition 0.1-6 wt.-% $Na_2O$, containing apatite and calcium zirconium phosphate as main crystal phases and a glass phase as an auxiliary component and, if appropriate, a sodium zirconium phosphate phase as an additional auxiliary component, wherein the main crystal phases jointly make up at least 35 wt.-% and the auxiliary components may each make up 5-15 wt.-%.

Furthermore, the vitreous-crystalline material may additionally contain 0.1-6 wt.-% magnesium oxide and/or potassium oxide and in addition, if appropriate, the respective phases as an auxiliary component.

$Na_2O$, MgO and/or $K_2O$ are preferably contained in amounts ranging between 1 and 6 wt.-%. The percentage of the respective secondary crystal phase sodium zirconium phosphate may range between 5 and 10 wt.-%.

In general, the terms "glass ceramics" and "vitreous-crystalline material" used herein cannot always be clearly defined. Both crystalline and vitreous or X-ray-amorphous phases are provided in a thoroughly mixed state. It is of no importance for the present invention whether one phase is located adjacent to the other or one phase encloses the other.

The term "main crystal phase" as used herein refers to a crystalline phase which is contained in at least twice the amount of a secondary phase, concentrations of approximately 15% and below, preferably below 10 wt.-%, being referred to as secondary phases.

It has now been found that the vitreous-crystalline material, although it contains apatite, has a very great solubility resistance, even in a slightly acid medium as is observed during inflammatory reactions, i.e. pH=6.0 [Berger et al., Hydroxyapatite's solubility may cause loosening of coated implants, Bioceramics Vol. 13, edited by Santro Giannini and Antonio Moroni (Proceedings of the 13$^{th}$ International Symposium on Ceramics in Medicine); Trans Tech Publ. Ltd, Swiss, 2000, 111-114]. This means that contrary to the current trend of an increase in the solubility of apatites by additional crystal phases or residual glass components, the combination according to the invention surprisingly shows a decrease of the material's solubility.

Furthermore, it has surprisingly been found that after the material (the vitreous-crystalline material) had been stored in deionised water, the material's surface properties change in the direction of physiological pH values (7.4) after an initial alkaline reaction.

The thermal coefficient of expansion of the material ranges between 1.4 and 6*10$^{-6}$ degree-1 in the range between 27° C. and 300, 400, 600 or 800° C.

Another feature of the material is that it has a total solubility of 4 to 5.5 mg/l if the test is carried out in 0.2M TRIS-HCl buffer solution at pH=7.4, T=37° C., using a grain size fraction of 315-400 μm, the duration of the test being 120 h and the ratio of surface (sample) to volume (solvent) being 5 cm$^{-1}$.

Another feature of the material is that already after having been stored in water (144 h) at 37° C., the surface of the material is adjusted in such a way that physiological pH values of approximately 7.4 can be determined. If the water bath temperature is increased, the surface change is accelerated accordingly.

If the vitreous-crystalline material, which is both bioactive and long-term stable, after its production from the melting phase, was ground and, if necessary, sieved into a granulated material with a particle size ranging between 53 and 350 μm, a blasting of the relevant surface of a metal implant may be carried out using said granulated material as blasting material. Owing to tribochemical reactions, particles of the granulated material are incorporated into the surface and, at the same time, a roughening of the surface is achieved. Since the new vitreous-crystalline material is bioactive and has, at the same time, an excellent long-term stability, the process of incorporation of the implant into the body is considerably accelerated and the risk of complications can be kept at a lower level compared to the known blasting materials.

The invention also relates to a blasting material for metallic implants characterised by a bioactive vitreous-crystalline material, consisting of 15-45 wt.-% CaO, 40-45 wt.-% $P_2O_5$, 10-40 wt.-% $ZrO_2$ and 0.7-3.5 wt.-% fluoride, containing apatite and calcium zirconium phosphate as main crystal phases and a glass phase as an auxiliary component, wherein the main crystal phases jointly make up at least 35 wt.-% and the auxiliary components make up 5-15 wt.-% and wherein all of the percentage data are expressed in relation to the total weight of the vitreous-crystalline material and the particle size of the vitreous-crystalline material ranges between 53 and 350 μm.

An embodiment of the blasting material may be such that the vitreous-crystalline material additionally contains 0.1 to 6 wt.-% $Na_2O$ and in addition, if appropriate, a sodium zirconium phosphate phase as an auxiliary component.

Another embodiment of the blasting material may be such that a part of the (1) bioactive vitreous-crystalline material is replaced by (2) a long-term stable biocompatible glass ceramic material which contains apatite and wollastonite as main crystal phases (e.g. in accordance with patent DD 247574) and/or (3) a resorbable biocompatible glass ceramic material which contains apatite, wollastonite and $Ca_7Mg_2P_2O_{24}$ as main crystal phases (e.g. in accordance with DE 197 44 809 C1, Example 2, or EP-B-0541546, Composition h).

Advantageously, the blasting material according to the mentioned embodiments has the following particle sizes:
Material (1) has a particle size between 53 and 350 μm,
Material (2) has a particle size between 70 and 315 μm, and
Material (3) has a particle size between 53 and 250 μm, in particular 100 and 150 μm.

The particle sizes were determined by means of laser granulometry.

The implant base body consists of any common implant metal, preferably a material selected from the group consisting of titanium, titanium alloys, special steel, Co—Cr special steel and Co—Cr—Mo alloys.

The vitreous-crystalline material is produced by preparing a mixture of suitable substances, i.e. using 15-45 wt.-% CaO, 40-45 wt.-% $P_2O_5$, 10-40 wt.-% $ZrO_2$ and 0.7-3.5 wt.-% fluoride. Preferably, the fluoride is added in the form of $CaF_2$. The aforesaid components of the mixture are combined with one another, subjected to suitable, mostly multi-stage thermal treatment programmes (holding stages in the range between 400 and 1,500° C.) and melted at between 1,550 and 1,650° C. in a suitable crucible material, preferably consisting of a Pt/Rh alloy. The melt is poured and once it has solidified the mass is cooled down to room temperature in air (spontaneous cooling) or in a cooling furnace, depending on its intended use. Finally, the material is ground.

The invention will hereinafter be explained in more detail by means of examples. All percentages are by weight, unless stated otherwise.

EXAMPLE 1

Production of the Vitreous-Crystalline Material Apatite1/CZP1

A mixture having the following composition is prepared (Code: Apatite/CZP1):
25.88 CaO
28.44 $ZrO_2$
43.68 $P_2O_5$
5.00 $CaF_2$.

In doing so, the amount of CaO can be added in the form of 62.79 $CaHPO_4$ and the required amount of $P_2O_5$ can be incorporated in the form of 10.51 ml of an 85% $H_3PO_4$. First, $CaHPO_4$, $ZrO_2$ and $CaF_2$ are thoroughly mixed, then the phosphoric acid is added, the mixture is left to react and subsequently ground in a mortar, the process including holding stages at 120° C. and 170° C. lasting 4 hours each and intended to dry the product. The reaction mixture obtained in this way is filled into a Pt/Rh crucible, heated up to 400° C., held at this temperature for 1 hour, heated up to 800° C., held at this temperature for 1 hour, cooled and ground in a mortar. The material pre-treated in this way is now melted in a Pt/Rh crucible, the melting process including holding times of 15 min at 800, 1,000, 1,300, 1,500 and finally 1,600° C. respectively, and poured onto a steel plate at room temperature.

Once the melt had solidified, part of the material obtained was milled in an agate mill and particles below 43 μm were separated by sieving and analysed by means of X-ray diffractography. The result (X-ray diffractogram) shows that the crystal phases apatite (fluoroapatite/hydroxyapatite) and calcium zirconium phosphate [$CaZr_4(PO_4)_6$] are clearly detectable in the vitreous-crystalline product.

The remaining part of the solidified melt is comminuted until a particle size of 60-350 μm is achieved.

EXAMPLE 2

Production of the Vitreous-Crystalline Material Apatite1/CZP2

A mixture is prepared according to the instructions of Example 1, except that sodium oxide is added as an additional component (Code: Apatite/CZP2). Specifically, the following components are mixed:

59.93 $CaHPO_4$
27.10 $ZrO_2$
3.42 $Na_2O$
5.00 $CaF_2$ and
9.56 ml of an 85% $H_3PO_4$.

Processing was done as in Example 1. At the end of the last temperature holding stage, the melt was poured out of the crucible onto a steel plate.

Once the melt had solidified, part of the material obtained was milled in an agate mill and particles below 43 μm were separated by sieving and analysed by means of X-ray diffractography. The result (X-ray diffractogram) shows that the crystal phases apatite (fluoroapatite/hydroxyapatite) and calcium zirconium phosphate [$CaZr_4(PO_4)_6$] and sodium zirconium phosphate [$NaZr_2(PO_4)_3$] are detectable in the vitreous-crystalline product.

The remaining part of the solidified melt is comminuted until a particle size of 60-350 μm is achieved.

EXAMPLE 3

Coefficients of Expansion of Apatite/CZP1

A vitreous-crystalline material according to Example 1 was produced (Apatite/CZP1). The material is milled in a mill lined with zirconium oxide until a $D_{50}$-value of 8 μm was achieved. The ground material is combined with a 5% polyvinyl-alcohol (PVA) solution, the ratio of ground material to PVA solution being 90 to 10 wt.-%, and the mixture is compression-moulded into a rod applying a force of 4.7 kN. The resulting compact is sintered at a temperature of 1,050° C.

Then, the thermal coefficient of expansion (CE) of the relatively dense moulded body obtained in this way is determined:

| | |
|---|---|
| CE in the range of 27-400° C.: | $1.90 * 10^{-6}$ degree Celsius$^{-1}$ |
| CE in the range of 50-400° C.: | $1.86 * 10^{-6}$ degree Celsius$^{-1}$ |
| CE in the range of 30-300° C.: | $1.45 * 10^{-6}$ degree Celsius$^{-1}$ |
| CE in the range of 30-400° C.: | $1.88 * 10^{-6}$ degree Celsius$^{-1}$ |
| CE in the range of 30-600° C.: | $2.6 * 10^{-6}$ degree Celsius$^{-1}$ |
| CE in the range of 30-800° C.: | $3.2 * 10^{-6}$ degree Celsius$^{-1}$ |

EXAMPLE 4

Chemical Stability of Apatite/CZP1 in the Alkaline Range

A vitreous-crystalline material according to Example 1 is produced (Apatite/CZP1). Subsequently, the material is ground in a mortar until a particle size fraction of 315-400 μm is obtained.

The chemical stability of the granulated material obtained in this way is compared to those of a basic glass ($Ap40_{glass}$) and a glass ceramic made from said basic glass and based on apatite and wollastonite ($Ap40_{cryst.}$) [i.e. with a chemical composition corresponding to (wt.-%): 44.3 $SiO_2$; 11.3 $P_2O_5$; 31.9 CaO; 4.6 $Na_2O$; 0.19 $K_2O$; 2.82 MgO and 4.99 $CaF_2$]

First, the specific surface areas according to BET were determined using krypton as measuring gas. The following results were obtained:

| | |
|---|---|
| Apatite/CZP1: | 0.364 m$^2$/g |
| $Ap40_{glass}$: | 0.018 m$^2$/g |
| $Ap40_{cryst.}$: | 0.055 m$^2$/g. |

It can be seen that the material according to the invention has a certain open porosity compared to the basic glass and the glass ceramic made therefrom. These differences are taken into account in the solubility tests by adjusting the ratio of surface (sample) to volume of solvent (TRIS-HCl buffer solution) to a constant value of 5 cm$^{-1}$.

The solvent used was 0.2M TRIS-HCl buffer solution, pH=7.4, at 37° C. The samples were stored therein for 120 hours at a temperature of 37° C. Then the samples' total solubility was determined by determining the individual ions (Ca, P, Zr) in the solution by means of an ICP measurement. The following results were obtained:

| | |
|---|---|
| Apatite/CZP1: | 4.1-5.1 mg/l |
| $Ap40_{glass}$: | 318-320 mg/l |
| $Ap40_{cryst.}$: | 75.2-82.0 mg/l. |

The above values impressively demonstrate the high chemical stability of the material according to the invention under simulated physiological conditions, which is a known method for determining long-term stability in vitro.

EXAMPLE 5

Chemical Stability of Apatite/CZP1 in the Acid Range

The same procedure as in Example 4 is carried out, except that 0.2M TRIS-HCl buffer solution having a pH value of 6.0 and a temperature of 37° C. is used for measuring. In this way, an infection during the wound healing process or at a later stage causing the pH value to fall from the physiological value of 7.4 down into the acid range can be simulated.

The following total solubility values (Ca, P, Zr) were determined by means of ICP:

| | |
|---|---|
| Apatite/CZP1: | 16-19 mg/l |
| $Ap40_{glass}$: | 505-518 mg/l |
| $Ap40_{cryst.}$: | 117-125 mg/l. |

The above values impressively demonstrate the high chemical stability of the material used for the invention under simulated conditions corresponding to those during an inflammation reaction. According to the test results, the absolute solubility values of the material according to the invention increase to a much smaller extent than those of the basic glass and the glass ceramic based on apatite/wollastonite which rise quite dramatically.

EXAMPLES 6 TO 11

Metal implants based on titanium (Ti) and on a cobalt base alloy (Wisil) were treated with blasting material under the following conditions:
Blasting time per cm² surface area: 10-15 sec
Blasting pressure: 4 bar
Blasting distance: 1 cm
Blasting material:
a) Material according to Example 1, particle size 100-250 μm
b) Material according to Example 1, particle size 100-250 μm +Ap40, particle size 100-250 μm (amount: 30 wt.-%)
c) Material according to Example 1, particle size 100-250 μm +resorbable ceramic, particle size 53-150 μm.

The increase in roughness (in μm) of the surface area concerned was determined by scanning with a Hommel tester. The results are shown as mean values in the table below:

|  | Example | | | | | |
| --- | --- | --- | --- | --- | --- | --- |
|  | 6 Ti | 7 Wisil | 8 Ti | 9 Wisil | 10 Ti | 11 Wisil |
| Material a | 8.9 | 7.6 | — | — | — | — |
| Material b | — | — | 9.5 | 7.8 | — | — |
| Material c | — | — | — | — | 8.7 | 7.6 |

REM and Electron Beam Microanalysis:

When recording EDS spectra, an increase in the content of components consisting of vitreous-crystalline material or ceramic material (Ca, P, . . . ) was observed. Evidence was provided for the incorporation of particles into the metal surface.

An electrochemical analysis of the metal surfaces was carried out by recording I-E-curves (current-voltage). As far as Ti is concerned, a cathodic displacement of the zero current potential was observed, compared to an untreated Ti surface.

Now that the invention has been described:

We claim:

1. A blasting material for metallic implants comprising a bioactive vitreous-crystalline material comprising 15-45 wt.-% CaO, 40-45 wt.-% $P_2O_5$, 10-40 wt.-% $ZrO_2$ and 0.7-3.5 wt.-% fluoride, containing apatite and calcium zirconium phosphate as main crystal phases and a glass phase as an auxiliary component, wherein the main crystal phases jointly make up at least 35 wt.-% and the auxiliary components make up 5-15 wt.-% and wherein all of the percentage data are expressed in relation to the total weight of the vitreous-crystalline material and the particle size of the vitreous-crystalline material ranges between 53 and 350 μm.

2. A surface-treated metallic implant comprising a metallic implant base body which has on its surface a blasting material of claim 1.

3. The implant according to claim 2 wherein said implant has on its surface particles of a vitreous-crystalline material consisting of 23-39 wt.-% CaO, 40-45 wt.-% $P_2O_5$, 20-35 wt.-% $ZrO_2$ and 1-3 wt.-% fluoride.

4. The implant according to claim 2 wherein said implant has on its surface particles of vitreous-crystalline material additionally containing 0.1 to 6 wt.-% $Na_2O$ and additionally containing a sodium zirconium phosphate phase as an auxiliary component.

5. The implant according to claim 2 wherein said implant has on its surface particles of a vitreous-crystalline material additionally containing 0.1 to 6 wt.-% magnesium oxide or potassium oxide and, if appropriate, additionally containing the respective phases as an auxiliary component, or mixtures thereof.

6. The implant according to claim 2 wherein said implant has on its surface particles of a vitreous-crystalline material and shows one or several of the following parameters:

a total solubility ranging between 4 and 5.5 mg/l if the test is carried out in 0.2M TRIS-HCl buffer solution at pH =7.4, T =37° C., using a particle size fraction of 315-400 μm, the duration of the test being 120 hours and the ratio of sample surface to volume of solvent being 5 $cm^{-1}$, a thermal coefficient of expansion between 1.4 and 6*$10^{-6}$ $degree^{-1}$ in the range between 27° C. and 300, 400, 600 or 8000° C., stability in the pH range between 7.0 and 7.5.

7. The implant according to claim 2 wherein the blasting material further comprises (1) a long-term stable biocompatible glass ceramic material which contains apatite and wollastonite as main crystal phases, (2) a resorbable biocompatible glass ceramic material which contains apatite, wollastonite and $Ca_7Mg_2P_2O_{24}$ as main crystal phases, or (3) a mixture thereof.

8. The implant according to claim 7 wherein the percentage of the vitreous-crystalline material (1) ranges between 95 and 40 wt.-%, in relation to the total weight of the bioactive and biocompatible material.

9. The implant according to claim 8 wherein the percentage of the vitreous-crystalline material (1) ranges between 95 and 60 wt.-%, in relation to the total weight of the bioactive and biocompatible material.

10. The implant according to claim 2 wherein the blasting material further comprises a long-term stable biocompatible glass ceramic material which contains apatite and wollastonite as main crystal phases and the blasting material has a particle size ranging between 70 and 315 μm.

11. The implant according to claim 2 wherein the implant base body consists of a material selected from the group consisting of titanium, titanium alloys, special steel, Co—Cr special steel and Co—Cr—Mo alloys.

12. The implant according to claim 2, wherein the blasting material further comprises a resorbable biocompatible glass. ceramic material which contains apatite, wollastonite and $Ca_7Mg_2P_2O_{24}$ as main crystal phases and the material has a particle size ranging between 53 and 250 μm.

13. The blasting material according to claim 1 wherein the vitreous-crystalline material additionally contains 0.1 to 6 wt.-% $Na_2O$ and in addition contains a sodium zirconium phosphate phase as an auxiliary component.

14. The blasting material according to claim 1, further comprising (1) a long-term stable biocompatible glass ceramic material which contains apatite and wollastonite as main crystal phases, (2) a resorbable biocompatible glass ceramic material which contains apatite, wollastonite and $Ca_7Mg_2P_2O_{24}$ as main crystal phases, or (3) a mixture thereof.

15. The blasting material according to claim 1 wherein the blasting material further comprises a long-term stable biocompatible glass ceramic material which contains apatite and wollastonite as main crystal phases and the blasting material has a particle size ranging between 70 and 315 μm.

16. The blasting material according to claim 1, wherein the blasting material further comprises a resorbable biocompatible glass ceramic material which contains apatite, wollastonite and $Ca_7Mg_2P_2O_{24}$ as main crystal phases and the material has a particle size ranging between 53 and 250 μm.

* * * * *